(12) United States Patent
Siamon

(10) Patent No.: US 6,432,425 B1
(45) Date of Patent: *Aug. 13, 2002

(54) METHOD FOR TREATMENT WITH AN ANTIBACTERIAL AND ANTISEPTIC MIXTURE

(76) Inventor: Al Siamon, 2585 Lara La., Oceana, CA (US) 93445

( * ) Notice: Subject to any disclaimer, the term of this patent is extended or adjusted under 35 U.S.C. 154(b) by 0 days.

This patent is subject to a terminal disclaimer.

(21) Appl. No.: 09/657,995

(22) Filed: Sep. 8, 2000

(51) Int. Cl.⁷ .............. A61K 6/00; A61K 7/00; A61K 33/42; A61K 33/10; A01N 59/26; A01N 59/06
(52) U.S. Cl. ............ 424/401; 424/606; 424/686; 424/717
(58) Field of Search .............. 424/401, 47, 606, 424/686, 717; 514/769

(56) References Cited

U.S. PATENT DOCUMENTS

| | | | |
|---|---|---|---|
| 4,115,307 A | 9/1978 | McGilvery | |
| 4,307,089 A * | 12/1981 | Melloh et al. | 424/245 |
| 4,504,995 A | 3/1985 | Zippwald, Sr. | |
| 4,592,892 A * | 6/1986 | Ueno et al. | 422/28 |
| 4,740,366 A | 4/1988 | Winston et al. | |
| 4,828,621 A | 5/1989 | Siamon | |
| 4,851,212 A | 7/1989 | Winston et al. | |
| 5,434,182 A * | 7/1995 | Isaacs et al. | 514/546 |
| 5,552,078 A | 9/1996 | Carr et al. | |
| 5,635,462 A | 6/1997 | Fendler et al. | |
| 5,861,430 A | 1/1999 | Markonius | |
| 5,928,671 A | 7/1999 | Domenico | |
| 6,046,160 A | 4/2000 | Obi-Talbot | |
| 6,184,198 B1 * | 2/2001 | Siamon | 510/510 |
| 6,217,887 B1 * | 4/2001 | Beerse et al. | 424/401 |
| 6,225,279 B1 * | 5/2001 | Siamon | 510/510 |

* cited by examiner

*Primary Examiner*—Russell Travers
*Assistant Examiner*—Lauren Q. Wells
(74) *Attorney, Agent, or Firm*—Christopher Darrow; Greenberg Traurig LLP

(57) ABSTRACT

A formulation consisting of sodium bicarbonate, sodium carbonate and trisodium phosphate in aqueous solution is applied topically to treat an array of skin and tissue problems. The solution offers antibacterial, antiseptic, antifungal, and healing properties to skin scratches, cuts, sores, and fungus-infected nails. In addition, the solution dries as a thin film to the applied surfaces, continuously providing antibacterial, anti-fungal and antiseptic activity beneath the protective film long after it has been applied.

15 Claims, No Drawings

METHOD FOR TREATMENT WITH AN ANTIBACTERIAL AND ANTISEPTIC MIXTURE

BACKGROUND

1. Field of the Invention

The present disclosure relates to an antiseptic and antibacterial (generally antimicrobial) solution for use on human and animal tissue, and uses thereof.

2. Description of Related Art

The formulation of antibacterial and antiseptic solutions, having the ability to kill and/or reduce bacteria, fungus, and other microorganisms while healing wounds or infections, is of significant importance. To this effect, much research in the fields of antibacterial, anti-fungal, and antiseptic agents has been performed and has resulted in a plethora of solutions having a wide variety of formulations. However, while many of these complex compositions provide acceptable antibacterial, antiseptic, anti-fungal, and healing properties, these acceptable properties are often not employed together in one solution, despite the many exotic, expensive components employed. Furthermore, as these compositions do not typically remain on the skin, their antibacterial and anti-fungal properties are short-lived. Finally, many of these products have components that may be harmful to a user if used internally or ingested.

Therefore it would be advantageous to have a topical solution capable of having antiseptic and/or healing properties, while encompassing only a few readily available components. In addition, it would be advantageous for the solution to be nontoxic and not cause harm if used internally or ingested.

SUMMARY

In accordance with the present disclosure, a solution (liquid) that provides the above-mentioned advantages and its methods of use are provided. The present solution consists essentially of a mixture of sodium bicarbonate ($NaHCO_3$, CAS RN 144-55-8), sodium carbonate ($Na_2HCO_3$, CAS RN 497-19-8) and trisodium phosphate ($Na_3PO_4$, CAS RN 10101-89-0) formulated as an aqueous solution of those components, in various concentrations. The mixture of sodium bicarbonate, sodium carbonate, and trisodium phosphate, is present in the concentrations listed below, having a particular molar ratio.

In some embodiments, the solution (which is the above-described mixture dissolved in water) is applied topically to cuts, sores, infections, and skin irritations. The solution aids in encapsulating bacteria and microorganisms, and prevents their growth. The solution dries and forms a thin film or coating over the surface of the tissue, and thus continues to function long after it has been applied. The present solution has also been effective when used to kill fungus on fingernails and toenails and as a treatment for acne related infections.

In some embodiments, the solution is applied to sores, scratches and skin irritations (including psoriasis) to aid in the healing process. Furthermore, the solution when dry forms a thin film or protective barrier over the affected area and continues to protect the wound from contamination for an extended period of time after it has been applied.

In some embodiments, the solution is applied to acne. The solution helps in healing acne by forming a protective barrier over the infected skin follicle which blocks microorganisms from entering, thus eliminating the infection and scarring that might follow.

DETAILED DESCRIPTION

The following is a detailed description of illustrative embodiments. As these embodiments are described, various modifications or adaptations of the methods and or specific structures described may become apparent to those skilled in the art. All such modifications, adaptations, or variations that rely upon the teachings of the present disclosure, and through which these teachings have advanced the art, are considered to be within the spirit and scope of the present invention. Hence, these descriptions are not to be considered in a limiting sense, as it is understood that the present invention is in no way limited to the embodiments illustrated.

The present disclosure provides a method of use for a solution for human and animal tissue. For example, the solution is useful for preventing the growth of bacteria on human and animal tissue, including the skin. The solution has proven efficacy in encapsulating bacteria and viruses. In addition, the solution helps in healing sores, cuts, and skin irritations. It also aids in removing wrinkles, age spots, treating fungus on nails, and in treating psoriasis, a chronic skin inflammation. In addition, the solution provides a thin protective coating or film to skin surfaces. This protective coating remains on the skin and continues to prevent the growth of microorganisms, bacteria, and fungus, beneath the protective film, long after it has been applied.

For a description pertinent to the solution itself, see commonly invented application Ser. No. 09/098,042 "Cleaning Solution" filed Jun. 16, 1998, now U.S. Pat. No. 6,184, 198, and the corresponding International application Ser. No. PCT/99/1274 filed Jun. 7, 1999, published December 1999, both incorporated by reference herein in their entirety.

Advantageously, solutions in accordance with the present disclosure are formulated using a mixture of three well-known, readily available substances, sodium bicarbonate ($NaHCO_3$, CAS RN 144-55-8), sodium carbonate ($Na_2CO_3$, CAS RN 497-19-8) and trisodium phosphate ($Na_3PO_4$, CAS RN 10101-89-0). Each of these substances is essentially non-toxic and otherwise safe. Thus sodium bicarbonate is commonly known as baking soda and is often used as an additive in the preparation of foods as well as a cleaning agent. Sodium carbonate, commonly known as washing soda or sal soda, is a well-known cleaning additive or enhancer that also has uses, when in solution, as a skin cleanser for eczema. Finally, trisodium phosphate is well known as a water-softening agent as an ingredient in many common detergent formulations.

The antiseptic solution encompassed in certain embodiments is believed to gain its advantageous properties by employing a specific molar ratio of the above mentioned components. This specific molar ratio is then formulated in aqueous solutions of varying concentrations. Thus embodiments are aqueous solutions having various concentrations of a mixture of sodium bicarbonate (hereafter SB), sodium carbonate (hereafter SC) and trisodium phosphate (hereafter TSP) having a molar ratio of approximately 1:2.6:1.6. That is, for every mole of SB, 2.6 moles of SC and 1.6 moles of TSP are used to prepare the solutions.

In a typical nominally "full-strength" formulation, an amount of solution having a first concentration is prepared by combining approximately 910 grams of SB, approximately 1,930 grams of SC and approximately 2,270 grams of TSP in approximately 208 liters of water; the water used is, e.g., deionized water, softened water or water processed through a reverse osmosis (RO) system. Such a typical "full-strength" formulation of the first concentration is thus approximately 2.46 percent (%) solids or active ingredients. It will be understood that the quantity of "full-strength" solution described above is illustrative only and that other quantities having the same molar ratio and percent solids concentration can be readily prepared by one of ordinary skill in the art, for example 100 liters of the "full-strength" solution rather than 208 liters. In addition, it will be understood that while the specific molar ratio of the above components described has been found to be most effective for certain uses, other molar ratios are also effective for other uses. It has also been found that other solids concentrations of the "full-strength" formulation described above are also effective, for example, concentrations as high as approximately 2.7% or as low as approximately 2.2% are also found to be effective specifically as a antiseptic solution.

While "full-strength" formulations are useful as solutions, other formulations having concentrations less than that of the "full-strength" formulation are also found to be effective antibacterial and antiseptic agents. Thus a formulation having a second concentration is prepared by diluting a "full-strength" solution of the first concentration by approximately one-half. Hence, this "half-strength" formulation has a concentration that is 50% of the first concentration; as a result, such a typical formulation is approximately 1.23% solids. It should be noted that many other dilutions of the "full-strength" solution can be made and can be advantageously applied to treat skin problems; often a particular dilution of the "full-strength" formulation is determined by testing various concentrations to determine a "best" concentration. All of these alternate dilutions are thus also within the scope and spirit of the present invention. Finally it will be realized that while each of the aforementioned dilutions have been characterized as dilutions of the "full-strength" solution, any could be made directly by mixing together appropriate amounts of SB, SC and TSP in the proper molar ratio of 1:2.6:1.6, respectively.

In some embodiments, it has additionally been found advantageous to formulate the present solution in a particular manner. Thus in some embodiments, the appropriate amount of sodium bicarbonate (SB) is added to deionized, softened or RO water and stirred until dissolved. While SB is known to be quite soluble in water, it has been found to be advantageous to add the SB to water that has been warmed to between 30 to 40 degrees Celsius (° C.) to hasten dissolution. Once the SB is dissolved, the appropriate amount of sodium carbonate (SC) is added to the SB solution, again with stirring. Upon addition of the SC, it will be noted that a hazy solution is obtained, and even after prolonged stirring, the solution does not become fully clear. Finally the appropriate amount of trisodium phosphate (TSP) is added to the mixture of SB and SC, again with stirring. It will be noted that after addition of the TSP, in a short time (a few minutes) the mixture becomes clear, denoting a true solution of the three components.

One of ordinary skill in the art will realize that other methods of making the solution can be used. For example, the SC can be added to the water as the first step in preparing the solution. In addition, it is possible to use any one or several of the various hydrated forms of the several components rather than the anhydrous materials specified above. As known, where such hydrated forms are employed, the amount of hydrated material is adjusted to provide the appropriate "anhydrous equivalent weight" to obtain the appropriate molar ratio of approximately by 1:2.6:1.6. However, while these other methods of making the solution are within the scope and spirit of the present disclosure.

In some embodiments, the solution is formulated to be sprayed onto the affected area using a conventional sprayer. After the solution has been sprayed onto the affected area, it can be rubbed into the skin or tissue with fingers until dry. An applicator, cotton ball, etc is not required, as it might absorb the solution.

In addition to its action to suppress the growth of microorganisms such as fungus, the solution also exhibits activity against a wide variety of other microorganisms. For example, certain embodiments contemplate application to tissue surfaces to act as a antibacterial solution, eliminating some viable bacteria on contact, and essentially all the remaining bacteria upon drying as a film or thin coating. This result is believed to be due, at least in part, from the encapsulating properties of the film or coating that is formed on drying. In some embodiments, a second application of the solution is made to the tissue surface and allowed to dry, as described above. It has been found that where such a second application is made, the inhibition of re-growth of microorganisms, for example, bacteria and fungi, on the treated surface is extended. The film or coating formed upon drying is a hard, lubricious coating that has been found to be between approximately 2 to 10 microns thick. It is believed that the active agents, within the solution, combine to form an encapsulant that prevents the growth of microorganisms.

It should be apparent that a general-purpose antibacterial and antiseptic solution has been described that encompasses only three common, readily available components. It should also be apparent that the present solution can be formulated in a variety of concentrations so as to be able to provide antibacterial, anti-fungal, and antiseptic properties. In addition, it should be apparent that as each of the components of the solution are safe and essentially non-toxic material (even when taken internally), the mixture of these three components is also safe and essentially non-toxic.

Additionally, it should be apparent that the present solution has sequestering properties that enable it to be applied to a wide variety of skin and tissue problems. It should also be apparent that embodiments possess anti-fungal and antibacterial properties that extend by and through the formation of the thin film on drying.

What is claimed is:

1. A method of reducing or eliminating microorganisms on mammalian tissue comprising the acts of:
   topically applying a solution consisting essentially of sodium bicarbonate, sodium carbonate and trisodium phosphate having a molar ratio of approximately 1:2.6:1.6, to a surface of the mammalian tissue; and
   allowing the applied solution to dry wherein a film is formed thereof, thereby to reduce or eliminate the microorganisms from said surface of the tissue.

2. The method of claim 1, wherein said surface of the tissue is a skin surface having a sore, irritation, or scratch.

3. The method of claim 1, further comprising allowing said film to remain on said surface, thereby continuing to reduce or eliminate microorganisms underneath the film.

4. The method of claim 1, wherein said surface is a skin surface having acne, whereby the film blocks microorganisms from entering an infected skin follicle.

5. The method of claim 1, wherein the act of topically applying includes spraying.

6. The method of claim 1, further comprising the act of rubbing said solution into said surface of the tissue.

7. A method of reducing or eliminating fungal growth on mammalian tissue comprising the acts of;
   topically applying a solution consisting essentially of sodium bicarbonate, sodium carbonate and trisodium phosphate having a molar ratio of approximately 1:2.6:1.6, to the surface of the tissue; and allowing the applied solution to dry wherein a film is formed thereby to cover the fungus.

8. The method of claim 7 wherein said tissue is fingernails or toenails, wherein the fingernails or toenails have the fungal growth.

9. The method of claim 7, wherein the act of topically applying includes spraying.

10. The method of claim 7, further comprising the act of rubbing said solution into said tissue.

11. A method for promoting healing of mammalian skin, comprising the acts of:

applying to a surface of the skin a therapeutically effective solution, wherein said solution consists essentially of sodium bicarbonate, sodium carbonate and trisodium phosphate having a molar ratio of approximately 1:2.6:1.6; and allowing the applied solution to dry wherein a film is formed on the surface of the skin.

12. The method of claim 11, further comprising applying said solution repeatedly to said surface to promote healing.

13. The method of claim 11 wherein said surface has a sore, irritation, or scratch.

14. The method of claim 11, wherein the act of topically applying includes spraying.

15. The method of claim 11 wherein said skin has a disorder selected from the group consisting of psoriasis, acne, dermatitis, aging skin, and age spots.

* * * * *